(12) United States Patent
Kumar et al.

(10) Patent No.: US 9,815,772 B2
(45) Date of Patent: Nov. 14, 2017

(54) PROCESS FOR THE PREPARATION OF 2-AMINO-1,3-PROPANE DIOL COMPOUNDS AND SALTS THEREOF

(71) Applicant: Biocon Limited, Bangalore (IN)

(72) Inventors: Kothakonda Kiran Kumar, Karnataka (IN); Chandrashekar Aswathanarayanappa, Bannerghatta Road (IN); Dharshan Jakkali Chandregowda, Chikamaghur (IN); Chandrasekhar Duvva, Andhra Pradesh (IN); Venkata Srinivas Pullela, Andhra Pradesh (IN)

(73) Assignee: Biocon Limited, Bangalore (IN)

( * ) Notice: Subject to any disclaimer, the term of this patent is extended or adjusted under 35 U.S.C. 154(b) by 0 days.

(21) Appl. No.: 14/772,739

(22) PCT Filed: Mar. 4, 2014

(86) PCT No.: PCT/IB2014/059423
§ 371 (c)(1),
(2) Date: Sep. 3, 2015

(87) PCT Pub. No.: WO2014/136047
PCT Pub. Date: Sep. 12, 2014

(65) Prior Publication Data
US 2016/0009634 A1   Jan. 14, 2016

(30) Foreign Application Priority Data
Mar. 5, 2013  (IN) .............................. 951/CHE/2013

(51) Int. Cl.
C07C 213/08   (2006.01)
C07C 231/12   (2006.01)
C07C 227/06   (2006.01)

(52) U.S. Cl.
CPC .......... C07C 213/08 (2013.01); C07C 227/06 (2013.01); C07C 231/12 (2013.01)

(58) Field of Classification Search
None
See application file for complete search history.

(56) References Cited

U.S. PATENT DOCUMENTS 5,604,229 A * 2/1997 Fujita .................... C07C 215/10
                                                              514/252.1
2012/0184617 A1* 7/2012 Gidwani ............... C07C 215/28
                                                              514/554

FOREIGN PATENT DOCUMENTS

IN   WO2012146980   * 4/2012 .......... C07C 215/10

OTHER PUBLICATIONS

Tundo et al. J. Chem. Soc. Perkin Trans. 1, 1987, 2159.*

* cited by examiner

*Primary Examiner* — Clinton Brooks
(74) *Attorney, Agent, or Firm* — Schwegman Lundberg & Woessner, P.A.

(57) ABSTRACT

The present disclosure relates to processes for the preparation of 2-amino-1,3-propane diol compounds and their hydrochloride salts. Particularly, the present disclosure relates to processes for synthesizing 2-amino-2-(2-(4-octylphenyl)ethyl)-1,3-propanediol and its hydrochloride salt 2-amino-2-(2-(4-octylphenyl)ethyl)-1,3-propanediol hydrochloride respectively. The said process is safe, commercially feasible for large-scale synthesis and has improved efficacy along with many other advantages. The present disclosure also relates to the novel polymorphs of 2-amino-1,3-propane diol compound and its hydrochloride salt, where in 2-amino-1,3-propane diol compound is 2-amino-2-(2-(4-octylphenyl)ethyl)-1,3-propanediol, and its hydrochloride salt is 2-amino-2-(2-(4-octylphenyl)ethyl)-1,3-propanediol hydrochloride.

20 Claims, 3 Drawing Sheets

PROCESS FOR THE PREPARATION OF 2-AMINO-1,3-PROPANE DIOL COMPOUNDS AND SALTS THEREOF

PRIORITY APPLICATIONS

This application is a U.S. National Stage Filing under 35 U.S.C. 371 from International Application No. PCT/IB2014/059423, filed 4 Mar. 2014, and published as WO 2014/136047 on 12 Sep. 2014, which claims the benefit under 35 U.S.C. 119 to India Application No. 951/CHE/2013, filed on 5 Mar. 2013; which applications and publication are incorporated herein by reference in the entirety.

TECHNICAL FIELD

The present disclosure is in the field of pharmaceuticals. The disclosure relates to processes for the preparation of 2-amino-1,3-propane diol compounds and their hydrochloride salts. In particular, the present disclosure relates to processes for synthesizing 2-amino-2-(2-(4-octylphenyl)ethyl)-1,3-propanediol and its hydrochloride salt, 2-amino-2-(2-(4-octylphenyl)ethyl)-1,3-propanediol hydrochloride respectively. The said process is safe, commercially feasible for large-scale synthesis and has improved efficacy along with many other advantages.

BACKGROUND AND PRIOR ART OF THE DISCLOSURE

2-Amino-1,3-propane diol compounds are useful pharmaceuticals which are particularly used as immunosuppressants. 2-amino-2-(2-(4-octylphenyl)ethyl)-1,3-propanediol hydrochloride belongs to the same class of compounds with the common name as Fingolimod Hydrochloride. 2-amino-2-(2-(4-octylphenyl)ethyl)-1,3-propanediol hydrochloride (Fingolimod Hydrochloride) is an immunomodulator approved for the treatment of multiple sclerosis (MS) by US FDA in September 2010. Fingolimod hydrochloride is marketed with the trade name Gilenya®. Chemically, Gilenya® is 2-amino-2-(2-(4-octylphenyl)ethyl)-1,3-propanediol hydrochloride (Formula 1), having a Mol. Wt.: 380.44 and molecular formula: $C_{19}H_{34}NO_2Cl$.

(Formula 1)

Fingolimod Hydrochloride

U.S. Pat. No. 5,604,229 discloses the use of 2-amino-1,3-propane diol compounds as pharmaceuticals, in particular immunosuppressants. Said document discloses the synthesis of 2-amino-2-(2-(4-octylphenyl)ethyl)-1,3-propanediol hydrochloride (Fingolimod Hydrochloride) by various methods and also its use as an immunosuppressant. However, the disclosed synthetic routes for the preparation of Fingolimod Hydrochloride involve tedious column chromatographic purifications along with highly reactive reagents and reactions which are challenging to handle at commercial scales with safety.

US publication No. 2002/0072635 A1 discloses the process for the preparation of 2-amino-2-(2-(4-octylphenyl)ethyl)-1,3-propanediol hydrochloride involving the reduction of corresponding substituted phenone to the corresponding substituted benzyl alcohol and thereafter reductive deoxygenation of said substituted benzyl alcohol by tedious hydrogenation reaction.

WO 2010/055027 discloses various salts of 2-amino-2-(2-(4-octylphenyl)ethyl)-1,3-propanediol (Fingolimod) such as tartarate, lactate, benzoate, succinate, malonate, acetate, propionate salts and their corresponding polymorphic forms.

WO 2010/055028 A2 discloses the hydrate and crystalline polymorphs of 2-amino-2-(2-(4-octylphenyl)ethyl)-1,3-propanediol hydrochloride namely, Form-I, Form-II, Form-III.

WO 2011/009634 A2 discloses the process of pharmaceutically acceptable salts of Fingolimod such as ascorbate, succinate, oxalate, phosphate, mandelate, adipate salts and their corresponding polymorphic forms wherein the preparation of said salts involve freeze-drying technique.

Therefore, there is a need in the art to arrive at a robust and commercially viable process for the preparation of Fingolimod and/or its hydrochloride salt wherein the said process is safe, efficacious and does not involve any chromatographic purifications.

The present disclosure aims at overcoming the aforesaid drawbacks of the prior art.

STATEMENT OF THE DISCLOSURE

Accordingly, the present disclosure relates to a process for preparing 2-amino-2-(2-(4-octylphenyl)ethyl)-1,3-propanediol (Formula 6), said process comprising acts of:
a. reacting a compound of Formula 3 with diethylacetamido malonate (Formula 2) to obtain 2-(Acetylamino)-2-(2-(4-octylphenyl)ethyl)propanedioic acid diethyl ester (Formula 4), X = Cl, Br, I, OMs, OTs, OTf and
b. converting the 2-(Acetylamino)-2-(2-(4-octylphenyl)ethyl)propanedioic acid diethyl ester obtained in step (a) to obtain 2-amino-2-(2-(4-octylphenyl)ethyl)-1,3-propanediol (Formula 6), Formula 4

Formula 6

Formula 6 or
d. converting the 2-(Acetylamino)-2-(2-(4-octylphenyl) ethyl)propanedioic acid diethyl ester obtained in step (a) to N-(1,1-bis hydroxymethyl-3-(4-octyl phenyl)-propyl)-acetamide (Formula 5), followed by converting the N-(1,1-bis hydroxymethyl-3-(4-octyl phenyl)-propyl)-acetamide (Formula 5) to 2-Acetamido-2-(4-octylphenethyl) propane-1,3-diyl diacetate (Formula 5a), followed by hydrolysis of the Acetamido-2-(4-octylphenethyl) propane-1,3-diyl diacetate (Formula 5a) to obtain 2-amino-2-(2-(4-octylphenyl)ethyl)-1,3-propanediol (Formula 6);

or
c. converting the 2-(Acetylamino)-2-(2-(4-octylphenyl) ethyl)propanedioic acid diethyl ester obtained in step (a) to N-(1,1-bis hydroxymethyl-3-(4-octyl phenyl)-propyl)-acetamide (Formula 5), followed by hydrolysis of the N-(1,1-bis hydroxymethyl-3-(4-octyl phenyl)-propyl)-acetamide to obtain 2-amino-2-(2-(4-octylphenyl)ethyl)-1,3-propanediol (Formula 6), a polymorphic form A of 2-amino-2-(2-(4-octylphenyl) ethyl)-1,3-propanediol (Formula 6), obtained by the above process, having XRPD 2θ values of: 3.876, 5.744, 7.739, 11.65, 14.886, 15.356, 16.774, 17.65, 18.008, 18.963, 19.473, 20.845, 21.626, 23.431, 24.643, 27.389, 27.894, 30.566, 31.421, 34.267, 35.01, 35.5, 38.756, 42.214, 43.767, 46.201, 48.026, 50.269 and 52.314; and a polymorphic form Y of 2-amino-2-(2-(4-octylphenyl)ethyl)-1,3-propanediol hydrochloride (Formula 1), obtained by the above process, having XRPD 2θ values of: 3.549, 5.185, 5.832, 7.052, 8.62, 9.305, 10.625, 12.149, 12.82, 14.163, 14.713, 15.174, 15.61, 16.374, 17.329, 17.749, 18.254, 18.698, 19.255, 19.948, 20.879, 21.389, 22.248, 22.578, 22.838, 23.527, 24.449, 24.953, 25.847, 26.139, 27.127, 28.094, 28.604, 29.47, 29.697, 31.786, 32.24, 33.147, 36.955 and 44.474.

BRIEF DESCRIPTION OF THE
ACCOMPANYING FIGURES

In order that the disclosure may be readily understood and put into practical effect, reference will now be made to exemplary embodiments as illustrated with reference to the accompanying figures. The figure together with a detailed description below, are incorporated in and form part of the specification, and serve to further illustrate the embodiments and explain various principles and advantages, in accordance with the present disclosure, where.

DETAILED DESCRIPTION OF THE DISCLOSURE

The present disclosure relates to a process for preparing 2-amino-2-(2-(4-octylphenyl)ethyl)-1,3-propanediol (Formula 6), said process comprising acts of:

a. reacting a compound of Formula 3 with diethylacetamido malonate (Formula 2) to obtain 2-(Acetylamino)-2-(2-(4-octylphenyl)ethyl)propanedioic acid diethyl ester (Formula 4);

X = Cl, Br, I, OMs, OTs, OTf and b. converting the 2-(Acetylamino)-2-(2-(4-octylphenyl) ethyl)propanedioic acid diethyl ester obtained in step (a) to obtain 2-amino-2-(2-(4-octylphenyl)ethyl)-1,3-propanediol (Formula 6);

or c. converting the 2-(Acetylamino)-2-(2-(4-octylphenyl) ethyl)propanedioic acid diethyl ester obtained in step (a) to N-(1,1-bis hydroxymethyl-3-(4-octyl phenyl)-propyl)-acetamide (Formula 5), followed by hydrolysis of the N-(1,1-bis hydroxymethyl-3-(4-octyl phenyl)-propyl)-acetamide to obtain 2-amino-2-(2-(4-octylphenyl)ethyl)-1,3-propanediol (Formula 6);

or d. converting the 2-(Acetylamino)-2-(2-(4-octylphenyl) ethyl)propanedioic acid diethyl ester obtained in step (a) to N-(1,1-bishydroxymethyl-3-(4-octyl phenyl)-propyl)-acetamide (Formula 5), followed by converting the N-(1,1-bis hydroxymethyl-3-(4-octyl phenyl)-propyl)-acetamide (Formula 5) to 2-Acetamido-2-(4-octylphenethyl)propane-1,3-diyl diacetate (Formula 5a), followed by hydrolysis of the Acetamido-2-(4-octylphenethyl) propane-1,3-diyl diacetate (Formula 5a) to obtain 2-amino-2-(2-(4-octylphenyl)ethyl)-1,3-propanediol (Formula 6).

Formula 4 → Formula 5 → Formula 5a → Formula 6

In an embodiment of the present disclosure, the reaction of step (a) of the process as disclosed above is carried out in presence of solvent selected from a group comprising toluene, xylene, heptanes, hexanes, diethyl ether, methyl tertiary butyl ether and tetrahydrofuran or any combination thereof; and further comprises adding reagent selected from a group comprising alkaline metal carbonate and alkaline earth metal carbonate or a combination thereof.

In another embodiment of the present disclosure, volume of the solvent ranges from about 1 to about 30 volumes; and wherein the alkaline metal carbonate and alkaline earth metal carbonate is selected from a group comprising lithium carbonate, sodium carbonate, potassium carbonate, cesium carbonate, magnesium carbonate, calcium carbonate and barium carbonate.

In yet another embodiment of the present disclosure, the step (a) of the process as disclosed above is carried out at temperature ranging from about 10° C. to about 160° C. and for a time period ranging from about 3 hours to about 24 hours.

In still another embodiment of the present disclosure, the conversion of step (b) or step (c) or step (d) of the process as disclosed above is carried out in presence of a reagent in a solvent, wherein the solvent is a C1 to C4 lower chain alcohol and wherein the reagent is selected from a group comprising alkaline earth metal borohydride and alkaline earth metal alkoxy borohydride or a combination thereof.

In still another embodiment of the present disclosure, the C1-C4 lower chain alcohol is selected from a group comprising methanol, ethanol, n-propanol, isopropanol, n-butanol, 2-butanol, tertiary butanol, tetrahydrofuran, toluene, water, diethyl ether, methyl tertiary butyl ether or any combination thereof, having volume ranging from about 2 to about 30 volumes; wherein the alkaline earth metal borohydride is selected from a group comprising magnesium borohydride, calcium borohydride, sodium borohydride and barium borohydride; and wherein the alkaline earth metal alkoxy borohydride is selected from a group comprising magnesium triacetoxy borohydride, calcium triacetoxy borohydride and barium triacetoxy borohydride.

In still another embodiment of the present disclosure, the reagent is a combination of alkaline metal borohydride and a salt selected from a group comprising barium sulphate, barium chloride, magnesium sulphate, calcium acetate, calcium chloride, magnesium chloride and magnesium acetate or any mixture of salt thereof.

In still another embodiment of the present disclosure, the conversion of step (b) or step (c) or step (d) of the process as disclosed above is carried out at temperature ranging from about −5° C. to about 110° C.; pH ranging from about 1 to about 14; and wherein said pH range is achieved using solution selected from acid solution, base solution or a combination thereof.

In still another embodiment of the present disclosure, the acid solution is selected from a group comprising hydrochloric acid and acetic acid or a combination thereof and wherein the base solution is selected from a group comprising lithium hydroxide, sodium hydroxide, potassium hydroxide, magnesium hydroxide, calcium hydroxide and barium hydroxide or any combination thereof.

In still another embodiment of the present disclosure, the reaction of steps (a), (b), (c) and (d) of the process as disclosed above optionally comprises a phase transfer catalyst.

In still another embodiment of the present disclosure, the phase transfer catalyst is tetra alkyl ammonium halide; and wherein said tetra alkyl ammonium halide is selected from a group comprising tetramethyl ammonium bromide, tetraethyl ammonium bromide, tetrabutyl ammonium bromide and tetrabutyl ammonium iodide or any combination thereof.

In still another embodiment of the present disclosure, the hydrolysis is carried out either in presence of:
a. an inorganic base solution; or
b. hydrochloric acid followed by pH adjustment with base selected from a group comprising sodium hydroxide, lithium hydroxide, potassium hydroxide, magnesium hydroxide.

In still another embodiment of the present disclosure, the inorganic base is selected from a group comprising lithium hydroxide, sodium hydroxide, potassium hydroxide, magnesium hydroxide, calcium hydroxide and barium hydroxide or any combination thereof.

In still another embodiment of the present disclosure, addition of the inorganic base solution or the hydrochloric acid is followed by refluxing for a time period ranging from about 0.5 hours to about 24 hours.

In still another embodiment of the present disclosure, the conversion of 2-(Acetylamino)-2-(2-(4-octylphenyl)ethyl) propanedioic acid diethyl ester to 2-amino-2-(2-(4-octylphenyl)ethyl)-1,3-propanediol and the hydrolysis of N-(1,1-bis hydroxymethyl-3-(4-octyl phenyl)-propyl)-acetamide to 2-amino-2-(2-(4-octylphenyl)ethyl)-1,3-propanediol further comprises optional steps of adding solvent, stirring, filtration and drying.

In still another embodiment of the present disclosure, the 2-amino-2-(2-(4-octylphenyl)ethyl)-1,3-propanediol obtained is crystalline in nature and is designated as polymorph A.

In still another embodiment of the present disclosure, the process as disclosed above further comprises converting 2-amino-2-(2-(4-octylphenyl)ethyl)-1,3-propanediol (Formula 6) to 2-amino-2-(2-(4-octylphenyl)ethyl)-1,3-propanediol hydrochloride (Formula 1).

In still another embodiment of the present disclosure, the conversion is carried out by adding hydrochloric acid to the 2-amino-2-(2-(4-octylphenyl)ethyl)-1,3-propanediol in presence of a solvent at temperature ranging from about −25° C. to about 45° C.

In still another embodiment of the present disclosure, the hydrochloric acid is added in isopropanol; wherein the solvent is selected from a group comprising toluene, methyl acetate, ethyl acetate, isopropyl acetate, butyl acetate, acetonitrile, methyl isobutyl ketone and methyl ethyl ketone or a combination thereof; and wherein volume of the solvent ranges from about 2 volumes to about 25 volumes.

In still another embodiment of the present disclosure, the 2-amino-2-(2-(4-octylphenyl)ethyl)-1,3-propanediol hydrochloride obtained is crystalline in nature and is designated as polymorph Y.

In still another embodiment of the present disclosure, the 2-amino-2-(2-(4-octylphenyl)ethyl)-1,3-propanediol or the 2-amino-2-(2-(4-octylphenyl)ethyl)-1,3-propanediol hydrochloride is optionally purified and dried; and wherein the purification is carried out by re-crystallization in presence of solvent selected from group comprising toluene, methyl acetate, ethyl acetate, isopropyl acetate, butyl acetate, acetonitrile, methyl isobutyl ketone and methyl ethyl ketone or any combination thereof.

In still another embodiment of the present disclosure, volume of the solvent ranges from about 2 to about 30 volumes; wherein temperature for the purification of 2-amino-2-(2-(4-octylphenyl)ethyl)-1,3-propanediol ranges from about 10° C. to about 110° C.; and wherein temperature for the purification of 2-amino-2-(2-(4-octylphenyl)ethyl)-1,3-propanediol hydrochloride ranges from about −25° C. to about 50° C.

In still another embodiment of the present disclosure, the drying is carried out under vacuum at temperature ranging from about 20° C. to about 75° C.

In still another embodiment of the present disclosure, the compound of Formula 3 is represented by:

Formula 3

X = leaving group
Cl, Br, I, OMs, OTs, OTf

In still another embodiment of the present disclosure, the compound of Formula 3 is selected from a group comprising 1-(2-iodoethyl)-4-octylbenzene, 1-(2-bromoethyl)-4-octylbenzene, 1-(2-chloroethyl)-4-octylbenzene, 1-(2-ethylmesylate)-4-octylbenzene, 1-(2-ethyltosylate)-4-octylbenzene and 1-(2-ethyltriflate)-4-octylbenzene or any combination thereof.

The present disclosure further relates to a polymorphic form A of 2-amino-2-(2-(4-octylphenyl)ethyl)-1,3-propanediol (Formula 6), obtained by the above process, having XRPD 2θ values of: 3.876, 5.744, 7.739, 11.65, 14.886, 15.356, 16.774, 17.65, 18.008, 18.963, 19.473, 20.845, 21.626, 23.431, 24.643, 27.389, 27.894, 30.566, 31.421, 34.267, 35.01, 35.5, 38.756, 42.214, 43.767, 46.201, 48.026, 50.269 and 52.314.

The present disclosure further relates to a polymorphic form Y of 2-amino-2-(2-(4-octylphenyl)ethyl)-1,3-propanediol hydrochloride (Formula 1), obtained by the above process, having XRPD 2θ values of: 3.549, 5.185, 5.832, 7.052, 8.62, 9.305, 10.625, 12.149, 12.82, 14.163, 14.713, 15.174, 15.61, 16.374, 17.329, 17.749, 18.254, 18.698, 19.255, 19.948, 20.879, 21.389, 22.248, 22.578, 22.838, 23.527, 24.449, 24.953, 25.847, 26.139, 27.127, 28.094, 28.604, 29.47, 29.697, 31.786, 32.24, 33.147, 36.955 and 44.474.

The present disclosure overcomes the limitations of prior art to provide for a robust method for synthesizing Fingolimod and its hydrochloride salt, wherein said method is safe, commercially viable, efficacious and does not involve any chromatographic purifications. Hence, it is an objective of the present disclosure to provide improved methods for large-scale synthesis of Fingolimod and its hydrochloride salt.

In an embodiment of the present disclosure, the various chemical compounds and intermediates as disclosed herein are as follows:

Formula 1

2-amino-2-(2-(4-octylphenyl)ethyl)-1,3-propanediol hydrochloride
[Fingolimod Hydrochloride]

Formula 2

Diethylacetamido malonate

Formula 3

11
-continued

2-(Acetylamino)-2-(2-(4-octylphenyl)ethyl)propanedioic
acid diethyl ester Formula 4

N-(1,1-bis hydroxymethyl-3-(4-octyl phenyl)-propyl)-acetamide

Formula 5

(2-Acetamido-2-(4-octylphenethyl) propane-1,3-diyl diacetate)

Formula 5a

12
-continued 2-amino-2-(2-(4-octylphenyl)ethyl)-1,3-propanediol
[Fingolimod]

Formula 6

X = Cl, Br, I, OMs, OTs, OTf

Figure 1:
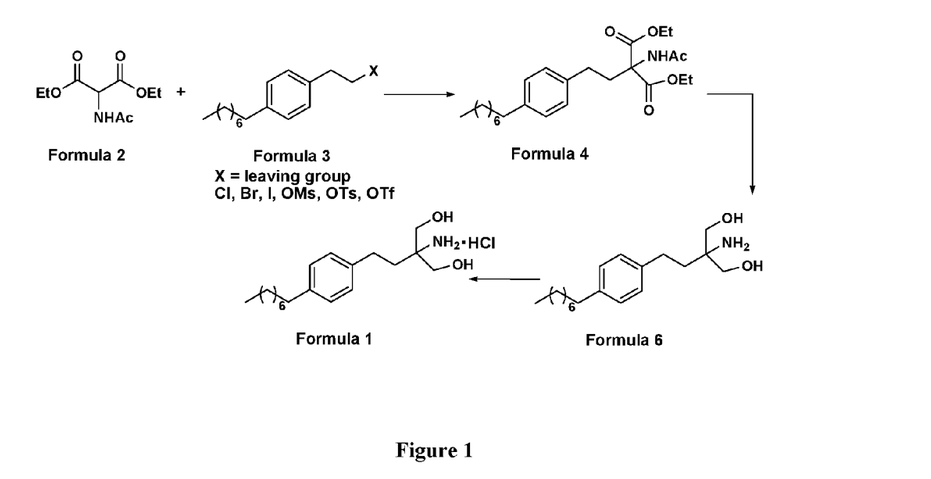
FIG. 1 depicts one of the embodiments of synthesizing fingolimod hydrochloride [2-amino-2-(2-(4-octylphenyl) ethyl)-1,3-propanediol hydrochloride] of the present disclosure.

In the first embodiment of the present disclosure, (Scheme 1 as represented below), fingolimod hydrochloride[2-amino-2-(2-(4-octylphenyl)ethyl)-1,3-propanediol hydrochloride] is synthesised by a process consisting of the following steps:

i. reacting 1-(2-iodoethyl)-4-octylbenzene (Formula 3) with Diethylacetamido malonate (Formula 2) under appropriate conditions to obtain corresponding coupled product: 2-(Acetylamino)-2-(2-(4-octylphenyl)ethyl)propanedioic acid diethyl ester (Formula 4);

ii. converting the 2-(Acetylamino)-2-(2-(4-octylphenyl) ethyl)propanedioic acid diethyl ester (Formula 4) to 2-amino-2-(2-(4-octylphenyl)ethyl)-1,3-propanediol (Formula 6) (Fingolimod free base) under suitable conditions in presence of suitable reagents;

iii. optionally, purifying the Fingolimod free base (Formula 6) and carrying out the step of drying after the purification;

iv. converting the 2-amino-2-(2-(4-octylphenyl)ethyl)-1,3-propanediol (Formula 6) (Fingolimod free base) to hydrochloride salt (i.e. Fingolimod Hydrochloride salt) (Formula 1); and v. optionally purifying the Fingolimod hydrochloride salt and carrying out the step of drying after the purification.

Scheme 1:

In an embodiment, FIG. 1 represents the above synthesis procedure which is detailed as follows:

(A) Reaction of 1-(2-iodoethyl)-4-octylbenzene [Formula 3] with Diethylacetamido malonate [Formula 2]

1-(2-Iodoethyl)-4-octylbenzene (Formula 3) is coupled with diethylacetamido malonate (Formula 2) in organic solvent selected from a group comprising toluene, xylene, heptanes, hexanes, diethyl ether, methyl tertiary butyl ether and tetrahydro furan or any mixture of said solvents thereof, at appropriate temperature in the presence of suitable reagents to obtain 2-(Acetylamino)-2-(2-(4-octylphenyl) ethyl)propanedioic acid diethyl ester (Formula 4). The volumes of solvents are about 1-30 volumes with respect to diethylacetamido malonate (Formula 2) and the temperature range is about 10° C. to 160° C. temperature.

The reagents used is selected from a group comprising alkaline metal carbonates and alkaline earth metal carbonates such as lithium carbonate, sodium carbonate, potassium carbonate, cesium carbonate, magnesium carbonate, calcium carbonate and barium carbonate or any mixture thereof. Optionally, phase transfer catalysts are also used to enhance the reactivity. Said phase transfer catalyst is selected from tetra alkyl ammonium halide such as tetramethyl ammonium bromide, tetraethyl ammonium bromide, tetrabutyl ammonium bromide and tetrabutyl ammonium iodide.

(B) Conversion of 2-(Acetylamino)-2-(2-(4-octylphenyl)ethyl)propanedioic acid diethyl ester [Formula 4] to 2-amino-2-(2-(4-octylphenyl)ethyl)-1,3-propanediol [Formula 6] (Fingolimod free base)

2-(Acetylamino)-2-(2-(4-octylphenyl)ethyl)propanedioic acid diethyl ester (Formula 4) is converted to 2-amino-2-(2-(4-octylphenyl)ethyl)-1,3-propanediol (Formula 6) (Fingolimod free base) by reacting in presence of suitable reagents in suitable solvent(s) at appropriate temperature. The solvents are selected from C1-C4 lower chain alcohols such as methanol, ethanol, n-propanol, isopropanol, n-butanol, 2-butanol, tertiary butanol, tetrahydrofuran, toluene, water, diethyl ether, methyl tertiary butyl ether or mixtures thereof. The volumes of the solvents ranges about 2-30 volumes and the temperature of the reaction range about −5° C. to 110° C. temperature.

The reagents used are selected from a group comprising alkaline earth metal borohydrides and alkaline earth metal alkoxy borohydrides such as magnesium borohydride, calcium borohydride, barium borohydride, sodium borohydride, magnesium triacetoxy borohydride, calcium triacetoxy borohydride and barium triacetoxy borohydride or any mixture thereof. In another aspect of the present disclosure, a combination of alkaline metal borohydride and a salt selected from barium sulphate, barium chloride, magnesium sulphate, calcium acetate, calcium chloride, magnesium chloride and magnesium acetate or any mixture of salt thereof, is also used as alternative reagents for the conversion.

In another aspect of the present disclosure, the pH of the reaction mixture is adjusted to acidic by adding acid solution selected from hydrochloric acid and acetic acid or a mixture thereof.

In yet another aspect of the present disclosure, pH of the reaction mixture is re-adjusted to basic to generate free base by adding basic solution selected from lithium hydroxide, sodium hydroxide, potassium hydroxide, magnesium hydroxide, calcium hydroxide and barium hydroxide or any mixtures thereof.

In another embodiment, an optional step is carried out wherein organic solvent is added and the reaction mixture is stirred for precipitation. The precipitate is isolated by filtration which comprises Fingolimod free base in solid form, and further optionally dried. Additionally, another optional step of purification is performed wherein, the Fingolimod free base is purified by re-crystallization in suitable solvent selected from a group comprising toluene, methyl acetate, ethyl acetate, isopropyl acetate, butyl acetate, acetonitrile, methyl isobutyl ketone and methyl ethyl ketone or any mixture thereof. The volumes of solvent used ranges about 2-25 volumes and the temperature range is about 10° C. to reflux temperature.

Figure 3:
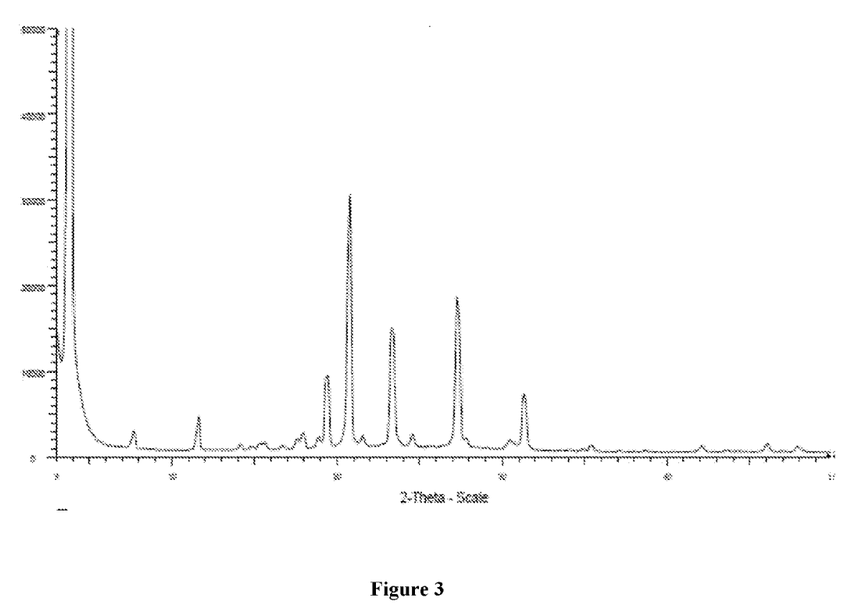
FIG. 3 depicts the X-ray diffraction pattern (PXRD) of Fingolimod polymorphic form A.

In yet another aspect of the present disclosure, the Fingolimod free base (Formula 6) is crystalline in nature and designated as polymorph A having 2θ values in XRPD as follows: 3.876, 5.744, 7.739, 11.65, 14.886, 15.356, 16.774, 17.65, 18.008, 18.963, 19.473, 20.845, 21.626, 23.431, 24.643, 27.389, 27.894, 30.566, 31.421, 34.267, 35.01, 35.5, 38.756, 42.214, 43.767, 46.201, 48.026, 50.269, 52.314 (FIG. 3).

(C) Conversion of 2-amino-2-(2-(4-octylphenyl) ethyl)-1,3-propanediol [Formula 6] (Fingolimod free base) to 2-amino-2-(2-(4-octylphenyl)ethyl)-1, 3-propanediol hydrochloride[Formula 1]

Fingolimod free base (Formula 6) is converted to its hydrochloride salt (Formula 1) by adding hydrochloric acid in isopropanol to Fingolimod (Formula 6) in the presence of suitable solvent selected from a group comprising toluene, methyl acetate, ethyl acetate, isopropyl acetate, butyl acetate, acetonitrile, methyl isobutyl ketone and methyl ethyl ketone or any mixture thereof, at temperature ranging about −25° C. to 45° C. In a preferred embodiment, the temperature ranges about −20° C. to 25° C., more preferably about −10° C. to 15° C. and most preferably about −5° C. to 10° C. The volumes of solvent used range about 2 to 25 volumes. Further, the precipitated material obtained after the completion of reaction is isolated and optionally dried under vacuum at temperature ranging from about 25° C. to 75° C.

Figure 4:
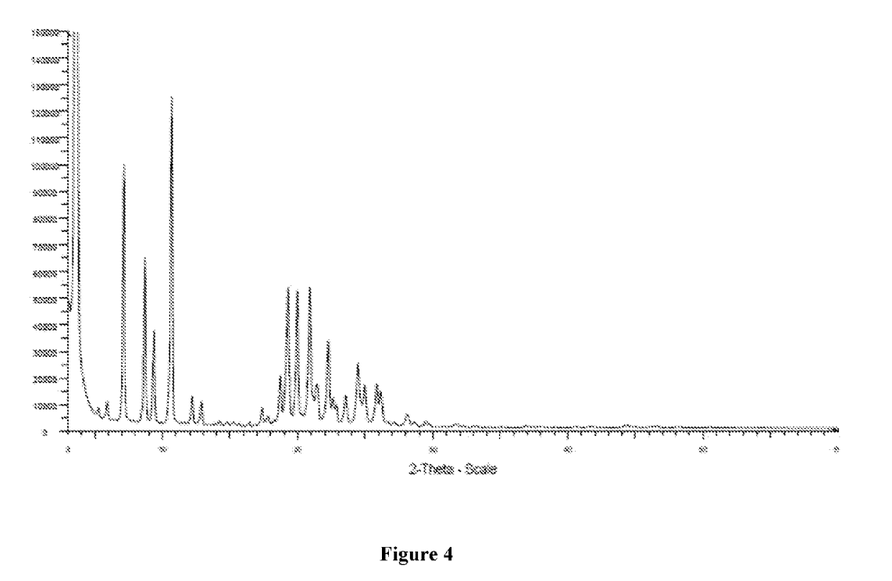
FIG. 4 depicts the PXRD of Fingolimod Hydrochloride polymorphic form Y.

In an embodiment of the present disclosure, Fingolimod hydrochloride (Formula 1) is crystalline in nature and is designated as polymorphic form Y having the peaks in XRPD at 2θ as follows: 3.549, 5.185, 5.832, 7.052, 8.62, 9.305, 10.625, 12.149, 12.82, 14.163, 14.713, 15.174, 15.61, 16.374, 17.329, 17.749, 18.254, 18.698, 19.255, 19.948, 20.879, 21.389, 22.248, 22.578, 22.838, 23.527, 24.449, 24.953, 25.847, 26.139, 27.127, 28.094, 28.604, 29.47, 29.697, 31.786, 32.24, 33.147, 36.955, 44.474 (FIG. 4).

In yet another aspect of the present disclosure, an optional step of purification is carried out wherein, the obtained Fingolimod hydrochloride is purified by recrystallization in a suitable solvent selected from a group comprising toluene, acetonitrile, methyl acetate, ethyl acetate, isopropyl acetate, butyl acetate, methanol, ethanol and isopropanol or any mixture thereof at temperature range of about −25° C. to 50° C. The optional purification step is further followed by drying the purified Fingolimod hydrochloride under vacuum at a temperature range of about 20° C. to 75° C.

Figure 2:
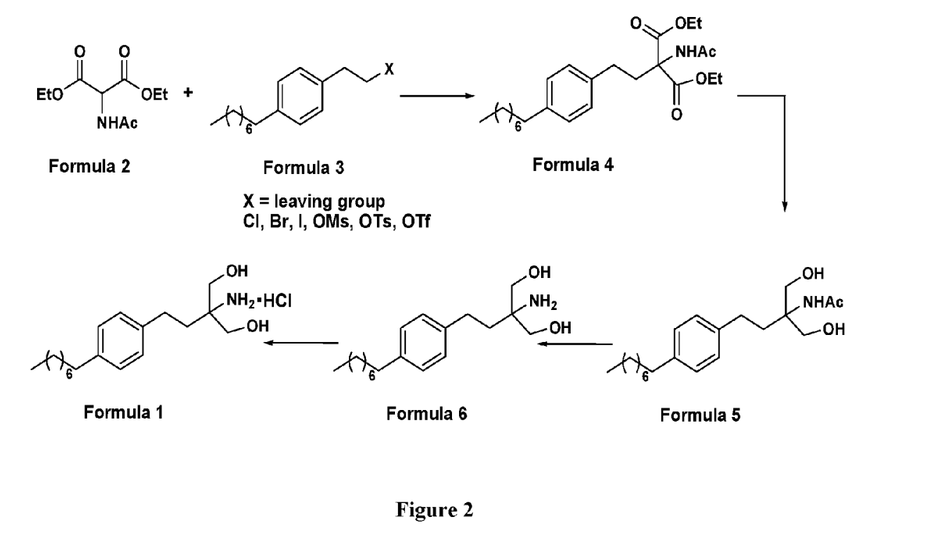
FIG. 2 depicts another embodiment of synthesizing fingolimod hydrochloride[2-amino-2-(2-(4-octylphenyl) ethyl)-1,3-propanediol hydrochloride] of the present disclosure.

In another exemplary embodiment of the present disclosure (Scheme 2 as represented below), Fingolimod hydrochloride is synthesised by a process comprising the following steps:

i. reacting 1-(2-iodoethyl)-4-octylbenzene (Formula 3) with Diethylacetamido malonate (Formula 2) under appropriate conditions to obtain corresponding coupled product 2-(Acetylamino)-2-(2-(4-octylphenyl)ethyl)propanedioic acid diethyl ester (Formula 4);
ii. converting the 2-(Acetylamino)-2-(2-(4-octylphenyl)ethyl)propanedioic acid diethyl ester (Formula 4) to N-(1,1-bis hydroxymethyl-3-(4-octyl phenyl)-propyl)-acetamide (Formula 5) under suitable conditions and in presence of suitable reagents;
iii. optionally, converting the N-(1,1-bis hydroxymethyl-3-(4-octyl phenyl)-propyl)-acetamide (Formula 5) to Formula 5a by protecting the hydroxyl groups;
iv. hydrolysing the N-(1,1-bis hydroxymethyl-3-(4-octyl phenyl)-propyl)-acetamide (Formula 5) (or) formula 5a to 2-amino-2-(2-(4-octylphenyl)ethyl)-1,3-propanediol (Fingolimod free base) (Formula 6) in the presence of base;
v. optionally, purifying Fingolimod free base (Formula 6) and carrying out the step of drying after the purification;
vi. converting the 2-amino-2-(2-(4-octylphenyl)ethyl)-1,3-propanediol (Fingolimod free base) (Formula 6) to its hydrochloride salt (i.e. Fingolimod Hydrochloride salt) (Formula 1); and
vi. optionally, purifying Fingolimod hydrochloride salt and carrying out the step of drying after the purification.

ates such as lithium carbonate, sodium carbonate, potassium carbonate, cesium carbonate, magnesium carbonate, calcium carbonate, barium carbonate or any mixture thereof. Optionally, phase transfer catalysts are also used to enhance the reactivity. Said phase transfer catalyst is selected from tetra alkyl ammonium halide such as tetrabutyl ammonium bromide, tetraethyl ammonium bromide, tetraethyl ammonium iodide and tetrabutyl ammonium iodide.

(B) Conversion of 2-(Acetylamino)-2-(2-(4-octylphenyl)ethyl)propanedioic acid diethyl ester [Formula 4] to N-(1,1-bis hydroxymethyl-3-(4-octyl phenyl)-propyl)-acetamide [Formula 5]

2-(Acetylamino)-2-(2-(4-octylphenyl)ethyl)propanedioic acid diethyl ester (Formula 4) is converted to N-(1,1-bis hydroxymethyl-3-(4-octyl phenyl)-propyl)-acetamide (Formula 5) by reaction with suitable reagents in suitable solvent, wherein the solvents are selected from C1-C4 lower chain alcohols such as methanol, ethanol, n-propanol, isopropanol, n-butanol, 2-butanol, tertiary butanol, tetrahydrofuran, toluene, water, diethyl ether, methyl tertiary butyl ether or any mixture thereof at appropriate temperature. The volumes of the solvents range from about 2-30 volumes and the temperature of the reaction ranges from about −5° C. to 110° C. temperature.

Scheme 2:

Formula 2    Formula 3    Formula 4

Formula 1    Formula 6    Formula 5

In an embodiment, FIG. 2 represents the above synthesis procedure which is detailed as follows:

(A) Reaction of 1-(2-iodoethyl)-4-octylbenzene [Formula 3] with Diethylacetamido malonate [Formula 2]

1-(2-Iodoethyl)-4-octylbenzene (Formula 3) is coupled with diethylacetamido malonate (Formula 2) in organic solvent selected from group comprising toluene, xylene, heptanes, hexanes, diethyl ether, methyl tertiary butyl ether and tetrahydrofuran or any mixture of said solvents thereof at appropriate temperature. The reaction is carried out in presence of suitable reagents to obtain 2-(Acetylamino)-2-(2-(4-octylphenyl)ethyl)propanedioic acid diethyl ester (Formula 4). The volumes of organic solvents used range from about 1-30 volumes and the temperature ranges from about 10° C. to 160° C. temperature.

The reagent used is selected from a group comprising alkaline metal carbonates and alkaline earth metal carbon- In an embodiment, the reagents used are selected from a group comprising alkaline earth metal borohydrides and alkaline earth metal alkoxy borohydrides such as magnesium borohydride, calcium borohydride, barium borohydride, sodium borohydride, magnesium triacetoxy borohydride, calcium triacetoxy borohydride and barium triacetoxy borohydride or any mixture thereof. Interestingly, usage of phase transfer catalyst in this step controls the formation of undesired by-products. Said phase transfer catalyst is selected from tetra alkyl ammonium halide such as tetrabutyl ammonium bromide, tetraethyl ammonium bromide, tetraethyl ammonium iodide and tetrabutyl ammonium iodide.

In another aspect of the present disclosure, a combination of alkaline metal borohydride and a salt selected from barium sulphate, barium chloride, magnesium sulphate, calcium acetate, calcium chloride, magnesium chloride and magnesium acetate or any mixture of salt thereof, is also used as alternative reagents for the conversion.

In another aspect of the present disclosure, pH of the reaction mixture is adjusted to acidic with acid solution selected from hydrochloric acid, acetic acid or a mixture thereof.

In yet another aspect of the present disclosure, pH of the reaction mixture is optionally re-adjusted to basic to generate free base by adding basic solution selected from lithium hydroxide, sodium hydroxide, potassium hydroxide, magnesium hydroxide, calcium hydroxide and barium hydroxide or any mixtures thereof.

(C) Hydrolysis of N-(1,1-bis hydroxymethyl-3-(4-octyl phenyl)-propyl)-acetamide [Formula 5] to 2-amino-2-(2-(4-octylphenyl)ethyl)-1,3-propanediol (Fingolimod free base) [Formula 6]

N-(1,1-bis hydroxymethyl-3-(4-octyl phenyl)-propyl)-acetamide (Formula 5) is hydrolysed to 2-amino-2-(2-(4-octylphenyl)ethyl)-1,3-propanediol (Fingolimod free base) (Formula 6) using inorganic base solution selected from a group comprising lithium hydroxide, sodium hydroxide, potassium hydroxide, magnesium hydroxide, calcium hydroxide and barium hydroxide. Optionally, organic solvent is also added and the reaction mixture is stirred to obtain a precipitate. The precipitate is isolated by filtration which comprises the material in solid form, and thereafter optionally dried to obtain Fingolimod free base. In yet another aspect, Fingolimod free base is optionally purified by re-crystallization in suitable solvent selected from a group comprising toluene, methyl acetate, ethyl acetate, isopropyl acetate, butyl acetate, acetonitrile, methyl isobutyl ketone, methyl ethyl ketone or any mixture thereof. The volumes of solvent used ranges from about 2-25 volumes and the temperature range is about 10° C. to reflux temperature.

In another alternate embodiment of the present disclosure, N-(1,1-bis hydroxymethyl-3-(4-octyl phenyl)-propyl)-acetamide (Formula 5) is hydrolysed to 2-amino-2-(2-(4-octylphenyl)ethyl)-1,3-propanediol (Fingolimod free base) (Formula 6) using hydrochloric acid followed by pH adjustment with sodium hydroxide.

In yet another embodiment of the present disclosure, formula 5 is converted to fully protected compound of Formula 5a (2-Acetamido-2-(4-octylphenethyl) propane-1,3-diyl diacetate), and subsequently the compound of Formula 5a is converted to Fingolimod free base (Formula 6) by one pot hydrolysis under suitable conditions. In formula 5a, R is selected from hydroxyl protecting groups wherein, R is C1-C4 alkyl, aryl, such as acetyl, benzoyl, and substituted aromatic moiety.

Formula 5a

In yet another embodiment of the present disclosure, the Fingolimod free base (Formula 6) is crystalline in nature and designated as polymorph A having 2θ values in XRPD as follows: 3.876, 5.744, 7.739, 11.65, 14.886, 15.356, 16.774, 17.65, 18.008, 18.963, 19.473, 20.845, 21.626, 23.431, 24.643, 27.389, 27.894, 30.566, 31.421, 34.267, 35.01, 35.5, 38.756, 42.214, 43.767, 46.201, 48.026, 50.269, 52.314 (FIG. 3).

(D) Conversion of 2-amino-2-(2-(4-octylphenyl)ethyl)-1,3-propanediol [Formula 6] to 2-amino-2-(2-(4-octylphenyl)ethyl)-1,3-propanediol hydrochloride[Formula 1]

Fingolimod free base (Formula 6) is converted to its hydrochloride salt (Formula 1) by adding hydrochloric acid in isopropanol to Fingolimod (Formula 6) in the presence of suitable solvent selected from a group comprising toluene, methyl acetate, ethyl acetate, isopropyl acetate, butyl acetate, acetonitrile, methyl isobutyl ketone and methyl ethyl ketone or any mixture thereof, at temperature ranging from about −25° C. to 45° C. In a preferred embodiment, the temperature ranges from about −20° C. to 25° C., more preferably from about −10° C. to 15° C. and most preferably from about −5° C. to 10° C. The volumes of solvent used ranges from about 2 to 25 volumes. Further, the precipitated material (Formula 6) formed after the reaction is isolated and optionally dried under vacuum at temperature ranging from about 25° C. to 75° C.

In an embodiment of the present disclosure, Fingolimod hydrochloride (Formula 1) material obtained by the above procedure is crystalline in nature and is designated as polymorph Y having the peaks in XRPD at 2θ: 3.549, 5.185, 5.832, 7.052, 8.62, 9.305, 10.625, 12.149, 12.82, 14.163, 14.713, 15.174, 15.61, 16.374, 17.329, 17.749, 18.254, 18.698, 19.255, 19.948, 20.879, 21.389, 22.248, 22.578, 22.838, 23.527, 24.449, 24.953, 25.847, 26.139, 27.127, 28.094, 28.604, 29.47, 29.697, 31.786, 32.24, 33.147, 36.955, 44.474 (FIG. 4).

In yet another embodiment of the present disclosure, Fingolimod hydrochloride is optionally purified by recrystallization in suitable solvent at temperature range of about −25° C. to 50° C. The solvent is selected from a group comprising toluene, acetonitrile, methyl acetate, ethyl acetate, isopropyl acetate, butyl acetate, methanol, ethanol and isopropanol or any mixture thereof. Further, optional purification is followed by drying under vacuum at about 20° C. to 75° C.

The technology of the instant disclosure is further elaborated with the help of following examples. However, the examples should not be construed to limit the scope of the disclosure.

EXAMPLES

Example 1

Preparation of 2-(Acetylamino)-2-(2-(4-octylphenyl) ethyl)propanedioic acid diethyl ester (Formula 4)

To a suspension of Diethyl acetamido malonate (DEAM) [Formula 2] (28.39 g) and Cesium Carbonate (189.13 g) in Toluene (300 mL), tetrabutyl ammonium Bromide (0.468 g) and 1-(2-iodoethyl)-4-octyl benzene [Formula 3] (50 g) in toluene (50 mL) is added under nitrogen atmosphere. The contents are heated to reflux and maintained for a time-period of about 3 hours-10 hours. After the reaction completion, the obtained mass is cooled to about 30° C. followed by addition of water (300 mL) and separation of formed layers. The organic layer is washed with water followed by brine and dried over sodium sulphate. The solvent is evaporated under reduced pressure to give a crude compound of formula 4 (59 g).

Example 2

Preparation of N-[1,1-bis hydroxymethyl-3-(4-octylphenyl)propyl]acetamide (Formula 5)

To 2-(acetylamino)-2-(2-(4-octylphenyl)ethyl)propanedioic acid diethyl ester (Formula 4) (58 g) in 50% aqueous IPA (Isopropyl Alcohol) (600 mL), tetrabutyl ammonium bromide (4.31 g) and Sodium borohydride (25.41 g) is added and the reaction mass is stirred for about 8 hours-24 hours at temperature of about 20° C. to 35° C. After the reaction completion, the pH is adjusted to about 6.0±0.5 by using 6N aqueous hydrochloric acid solution. The reaction mass is filtered through Buchner funnel to remove the solids and the filtrate is concentrated under reduced pressure to obtain a syrup. To the resulted syrup, water is added (116 mL) and the compound is extracted into ethyl acetate (2×174 mL). The organic layer is washed with water followed by brine solution followed by drying over sodium sulphate and thereafter evaporated under reduced pressure. The product is crystallised using pet ether to get the title compound of Formula 5 (27 g).

Example 3

Preparation of N-[1,1-bis hydroxymethyl-3-(4-octylphenyl)propyl]acetamide (Formula 5)

To 2-(acetylamino)-2-(2-(4-octyl phenyl)ethyl) propanedioic acid di ethyl ester (Formula 4) (58 g) in IPA (928 mL), Calcium Acetate (63.47 g) is added and the reaction mixture is stirred at temperature of about 10° C.-15° C. for about 30 min. Thereafter, Sodium Borohydride (25.41 g) is added and the reaction mass is stirred for a time-period of about 8 hours-12 hours at temperature of about 10° C.-15° C. The reaction completion is monitored by TLC (thin layer chromatography). The reaction mass is quenched with 1.5N HCl solution to attain a neutral pH. The reaction mass is filtered to remove the solids and the filtrate is subjected to evaporation under vacuum. Thereafter, water (116 mL) is added and the compound is extracted into ethyl acetate (2×174 mL). The organic layer is washed with water (2×174 mL). The organic layer is washed with brine solution (58 mL) and dried over sodium sulphate. The resultant is filtered and evaporated under reduced pressure to form syrup wherein the syrup represents the title compound of Formula 5 (38 g).

Example 4

Preparation of N-[1,1-bis hydroxymethyl-3-(4-octylphenyl)propyl]acetamide (Formula 5)

To 2-(acetylamino)-2-(2-(4-octylphenyl)ethyl)propanedioic acid diethyl ester (0.196 g) [Formula 4] in IPA (3.2 mL) and water (0.8 mL), $BaCl_2.2H_2O$ (0.332 g) is added and the reaction mixture is stirred for 10-15 minutes. The reaction mass is cooled to about 0° C. to 5° C. using ice bath. $NaBH_4$ (0.085 g) is added portion wise, followed by stirring for about 12 hours-16 hours at about 10° C. to 15° C. The reaction completion is monitored by TLC. The pH of the reaction mass is adjusted to neutral by using 1.5N HCl solution. The solid is filtered and the filtrate is subjected to evaporation under reduced pressure. To this, water (5 mL) is added and the compound is extracted into ethyl acetate (3×10 mL). The organic layer is washed with brine (2×5 mL) and dried over $Na_2SO_4$, filtered and evaporated under reduced pressure to get the compound of Formula 5 as off-white solid (0.13 g).

Example 5

Preparation of N-[1,1-bis hydroxymethyl-3-(4-octylphenyl)propyl]acetamide (Formula 5)

Lithium bromide (72.02 g) and $NaBH_4$ (25.41 g) are added to IPA (928 mL) and water (232 mL) at a temperature range of about 10° C.-15° C. The contents are stirred for about 2 hours at the said temperature. To the above mixture, 2-(acetylamino)-2-(2-(4-octylphenyl)ethyl) propanedioic acid diethyl ester (58 g) [Formula 4] is added and the reaction mixture is stirred for about 24 hours at temperature range of about 10° C.-15° C. The reaction completion is monitored by TLC. The pH of the reaction mass is adjusted to neutral by using 1.5N HCl solution. The solid obtained after the completion of reaction is filtered and the filtrate is subjected to evaporation. Water is added to the filtrate and the compound is extracted into ethyl acetate (2×174 mL). The organic layer is washed with water. The organic layer is washed with brine solution and dried over sodium sulphate followed by filteration and evaporation under reduced pressure to yield syrup containing the title compound (of Formula 5) as syrup crude (36 g). The obtained compound of Formula 5 is used without further purification.

Example 6

Preparation of (2-amino-2[2-(4-octylphenyl)ethyl] propane-1,3-diol (Fingolimod base; Formula 6)

N-[1,1-bis hydroxymethyl-3-(4-octylphenyl)propyl]acetamide (38 g) [Formula 5] in IPA (133 mL) and 6M HCl (133 mL) is taken and the contents are heated to reflux and the refluxing is maintained for about 2 hours. The reaction mass is cooled to about 40° C. and the IPA is evaporated under reduced pressure. Then, the pH of the reaction mass is adjusted to about 9-10 by using 25% NaOH solution and the product is extracted to ethyl acetate (3×114 mL). The organic layer is washed with water (114 mL) followed by saturated sodium chloride solution (2×38 mL), dried over sodium sulphate and concentrated under reduced pressure. The contents are cooled to about 0-2° C., the solids are stirred for about 1 hour and filtered. The wet cake is washed with chilled ethyl acetate (38 mL). The crude material is recrystallized using ethyl acetate to obtain Fingolimod base (Formula 6) in pure form (21.5 g).

Example 7

Preparation of (2-amino-2[2-(4-octylphenyl)ethyl] propane-1,3-diol (Fingolimod base; Formula 6)

N-(1hydroxy-2 hydroxylmethyl-3-(4-octyl phenyl)-propyl)-acetamide (38 g) [Formula 5] in IPA (114 mL) and 6N HCl (114 mL) are charged together. The contents are heated to about 80±5° C. and stirred for about 2 hours. The reaction mixture is cooled to about 10±5° C. and the pH is adjusted to about 9.5±0.5 by using 25% Sodium Hydroxide solution. 5 volumes of water is added and the reaction mixture is stirred for about 1 hour. The solids are filtered and the filtrate is recrystallized in ethyl acetate. The crude material is recrystallized using ethyl acetate to obtain Fingolimod base (Formula 6) in pure form (18.2 g) having the purity 99.5%.

Example 8

Preparation of (2-amino-2[2-(4-octylphenyl)ethyl] propane-1,3-diol (Fingolimod base; Formula 6)

To 2-(acetylamino)-2-(2-(4-octylphenyl)ethyl)propanedioic acid diethyl ester (0.50 g) [Formula 4] in Ethanol (8.5 mL) and water (2.0 mL), CaCl$_2$ (0.32 g) is added and the reaction mixture is stirred for about 10 minutes-15 minutes. The reaction mass is cooled to about 10° C.-15° C. using ice bath. NaBH$_4$ (0.21 g) is added portion wise and the reaction mixture is stirred for about 4 hours-20 hours at about 10-15° C. The reaction completion is monitored by TLC. To the reaction mass, 6M HCl (1.5 mL) is added and the reaction mass is heated to reflux. The refluxing is maintained for about 2 hours. After the disappearance of the starting material, the reaction mixture is cooled to about 10±5° C. and the pH is adjusted to about 9.5±0.5 by using 25% Sodium Hydroxide solution. 5 volumes of water is added followed by stirring for about 1 hour. The solids are filtered and the filtrate is recrystallized in ethyl acetate to obtain Fingolimod free base.

Example 9

Preparation of Fingolimod Hydrochloride (Formula 1) [as provided by Scheme 1 of the present disclosure]

Fingolimod base (21 g) [Formula 6] in ethyl acetate (63 mL), and HCl in IPA (15.75 mL) are charged together. The contents are stirred for about 1 hour at temperature of about 75±5° C. The contents are then cooled to about 25-30° C. and the cooling is maintained for about 1 h at 25-30° C. The suspension is further cooled to about 0-5° C. and the said cooling is maintained for about 1 hour. The obtained solid after cooling is filtered and washed with chilled ethyl acetate (21 mL) and suck dried for about 1 hour under reduced pressure. The resultant is further dried for about 8-10 h at temperature of about 20-75° C. to get title compound (Formula 1) as white solid (20 g) with the chromatographic purity 99.7%.

Example 10

Preparation of 2-Acetamido-2-(4-octylphenethyl) propane-1,3-diyl diacetate [Formula 5a]

N-(1hydroxy-2 hydroxylmethyl-3-(4-octyl phenyl)-propyl)-acetamide (38 g) [Formula 5] in Pyridine (129 mL) is taken and stirred for about 10-15 minutes. The reaction mass is cooled to about 0-5° C. using ice bath. Acetic anhydride (168 ml) is added at a temperature range of about 0-5° C. The reaction completion is monitored by TLC. The pH of the reaction mass is adjusted to neutral by using 5% HCl solution. The product is extracted into Ethyl acetate (135 ml). The organic layer is washed with about 100 ml water followed by about 60 ml brine solution. Thereafter, the organic layer is dried over anhydrous sodium sulphate, and then the solvent is completely distilled off under reduced pressure. The product is recrystallized in hexane to obtain the compound 2-Acetamido-2-(4-octylphenethyl) propane-1,3-diyl diacetate (formula 5a) as solid.

Example 11

Preparation of 2-Acetamido-2-(4-octylphenethyl) propane-1,3-diyl diacetate [Formula 5a]

Pyridine (6.0 mL) is added to N-(1hydroxy-2 hydroxylmethyl-3-(4-octyl phenyl)-propyl)-acetamide (2 g) [Formula 5] in MDC (12 ml), and the mixture is stirred for about 5 minutes. The reaction mass is cooled to about 0-5° C. using ice bath. Acetyl chloride (12 ml) is added at a temperature range of about 0-5° C. The reaction completion is monitored by TLC. The pH of the reaction mass is adjusted to neutral by using 5% HCl solution. The organic layer is washed with about 10 ml water followed by about 4 ml brine solution. The organic layer is dried over anhydrous sodium sulphate, and the solvent is completely distilled off under reduced pressure. The product is recrystallized in hexane to obtain the compound 2-Acetamido-2-(4-octylphenethyl) propane-1,3-diyl diacetate (formula 5a) as solid.

Example 12

Preparation of (2-amino-2-[2-(4-octylphenyl)ethyl] propane-1,3-diol (Fingolimod base) [Formula 6]

To 2-Acetamido-2-(4-octylphenethyl) propane-1,3-diyl diacetate (formula 5a) (4 g) in methanol (12 mL), LiOH solution (12 mL) is added and the contents are heated to reflux and maintained for about 2 hours. The reaction mass is cooled to about 40° C. and evaporated Methanol under reduced pressure. The product is extracted to ethyl acetate (2×10 mL). The organic layer is washed with water (about 8 mL) followed by saturated sodium chloride solution (about 4 mL), dried over sodium sulphate and concentrated under reduced pressure. The contents are cooled to about 0-2° C., and the solids are stirred for about 1 hour and filtered. The wet cake is washed with chilled ethyl acetate (about 2 mL). The crude material is recrystallized using ethyl acetate to obtain Fingolimod base (formula 6) with chromatographic purity of about 99.6%.

We claim:
1. A process for preparing 2-amino-2-(2-(4-octylphenyl) ethyl)-1,3-propanediol (Formula 6), said process comprising acts of:
   a. reacting a compound of Formula 3 with diethylacetamido malonate (Formula 2) to obtain 2-(Acetylamino)-2-(2-(4-octylphenyl)ethyl)propanedioic acid diethyl ester (Formula 4);

-continued

Formula 4

X = Cl, Br, I, OMs, OTs, OTf and b. converting the 2-(Acetylamino)-2-(2-(4-octylphenyl) ethyl)propanedioic acid diethyl ester obtained in step (a) to obtain 2-amino-2-(2-(4-octylphenyl)ethyl)-1,3-propanediol (Formula 6);

Formula 4

Formula 6 or c. converting the 2-(Acetylamino)-2-(2-(4-octylphenyl) ethyl)propanedioic acid diethyl ester obtained in step (a) to N-(1,1-bis hydroxymethyl-3-(4-octyl phenyl)-propyl)-acetamide (Formula 5), followed by hydrolysis of the N-(1,1-bis hydroxymethyl-3-(4-octyl phenyl)-propyl)-acetamide to obtain 2-amino-2-(2-(4-octylphenyl)ethyl)-1,3-propanediol (Formula 6);

Formula 4

Formula 5

-continued

Formula 6 or d. converting the 2-(Acetylamino)-2-(2-(4-octylphenyl) ethyl)propanedioic acid diethyl ester obtained in step (a) to N-(1,1-bis hydroxymethyl-3-(4-octyl phenyl)-propyl)-acetamide (Formula 5), followed by converting the N-(1,1-bis hydroxymethyl-3-(4-octyl phenyl)-propyl)-acetamide (Formula 5) to 2-Acetamido-2-(4-octylphenethyl) propane-1,3-diyl diacetate (Formula 5a), followed by hydrolysis of the Acetamido-2-(4-octylphenethyl) propane-1,3-diyl diacetate (Formula 5a) to obtain 2-amino-2-(2-(4-octylphenyl)ethyl)-1,3-propanediol (Formula 6)

wherein the reaction of step (a) comprises a phase transfer catalyst, and
wherein the process further comprises
  e. adding hydrochloric acid in isopropanol to 2-amino-2-(26-(4-octylphenyl)ethyl)-1,3-propanediol (Formula 6) in a solvent to yield 2-amino-2-(2-(4-octylphenyl-ethyl)-1,3-propanediol hydrochloride (Formula 1).

2. The process as claimed in claim 1, wherein the reaction of step (a) is carried out in presence of solvent selected from a group comprising toluene, xylene, heptanes, hexanes, diethyl ether, methyl tertiary butyl ether and tetrahydrofuran or any combination thereof; and further comprises adding reagent selected from a group comprising alkaline metal carbonate and alkaline earth metal carbonate or a combination thereof.

3. The process as claimed in claim 2, wherein volume of the solvent ranges from about 1 to about 30 volumes; and wherein the alkaline metal carbonate and alkaline earth metal carbonate is selected from a group comprising lithium carbonate, sodium carbonate, potassium carbonate, cesium carbonate, magnesium carbonate, calcium carbonate and barium carbonate.

4. The process as claimed in claim 1, wherein the step (a) is carried out at temperature ranging from about 10° C. to about 160° C. and for a time period ranging from about 3 hours to about 24 hours.

5. The process as claimed in claim 1, wherein the conversion of step (b) or step (c) or step (d) is carried out in presence of a reagent in a solvent, wherein the solvent is a C1 to C4 lower chain alcohol and wherein the reagent is selected from a group comprising alkaline earth metal borohydride and alkaline earth metal alkoxy borohydride or a combination thereof.

6. The process as claimed in claim 5, wherein the C1-C4 lower chain alcohol is selected from a group comprising methanol, ethanol, n-propanol, isopropanol, n-butanol, 2-butanol, tertiary butanol, tetrahydrofuran, toluene, water, diethyl ether, methyl tertiary butyl ether or any combination thereof, having volume ranging from about 2 to about 30 volumes; wherein the alkaline earth metal borohydride is selected from a group comprising magnesium borohydride, calcium borohydride, sodium borohydride and barium borohydride; and wherein the alkaline earth metal alkoxy borohydride is selected from a group comprising magnesium triacetoxy borohydride, calcium triacetoxy borohydride and barium triacetoxy borohydride.

7. The process as claimed in claim 5, wherein the reagent is a combination of alkaline metal borohydride and a salt selected from a group comprising barium sulphate, barium chloride, magnesium sulphate, calcium acetate, calcium chloride, magnesium chloride and magnesium acetate or any mixture of salt thereof.

8. The process as claimed in claim 1, wherein the conversion of step (b) or step (c) or step (d) is carried out at temperature ranging from about −5° C. to about 110° C.; pH ranging from about 1 to about 14; and wherein said pH range is achieved using solution selected from acid solution, base solution or a combination thereof.

9. The process as claimed in claim 8, wherein the acid solution is selected from a group comprising hydrochloric acid and acetic acid or a combination thereof; and wherein the base solution is selected from a group comprising lithium hydroxide, sodium hydroxide, potassium hydroxide, magnesium hydroxide, calcium hydroxide and barium hydroxide or any combination thereof.

10. The process as claimed in claim 1, wherein the phase transfer catalyst is tetra alkyl ammonium halide; and wherein said tetra alkyl ammonium halide is selected from a group comprising tetramethyl ammonium bromide, tetraethyl ammonium bromide, tetrabutyl ammonium bromide and tetrabutyl ammonium iodide or any combination thereof.

11. The process as claimed in claim 1, wherein the hydrolysis is carried out either in presence of:

a. an inorganic base solution; or
b. hydrochloric acid followed by pH adjustment with base selected from a group comprising sodium hydroxide, lithium hydroxide, potassium hydroxide, magnesium hydroxide.

12. The process as claimed in claim 11, wherein the inorganic base is selected from a group comprising lithium hydroxide, sodium hydroxide, potassium hydroxide, magnesium hydroxide, calcium hydroxide and barium hydroxide or any combination thereof.

13. The process as claimed in claim 11, wherein addition of the inorganic base solution or the hydrochloric acid is followed by refluxing for a time period ranging from about 0.5 hours to about 24 hours.

14. The process as claimed in claim 1, wherein the conversion of 2-(Acetylamino)-2-(2-(4-octylphenyl)ethyl) propanedioic acid diethyl ester to 2-amino-2-(2-(4-octylphenyl)ethyl)-1,3-propanediol and the hydrolysis of N-(1,1-bis hydroxymethyl-3-(4-octyl phenyl)-propyl)-acetamide to 2-amino-2-(2-(4-octylphenyl)ethyl)-1,3-propanediol further comprises the steps of adding solvent, stirring, filtration and drying.

15. The process as claimed in claim 1, wherein the 2-amino-2-(2-(4-octylphenyl)ethyl)-1,3-propanediol obtained is crystalline in nature and is designated as polymorph A.

16. The process as claimed in claim 1, wherein the solvent in step (e) is selected from a group comprising toluene, methyl acetate, ethyl acetate, isopropyl acetate, butyl acetate, acetonitrile, methyl isobutyl ketone and methyl ethyl ketone or a combination thereof; and wherein volume of the solvent ranges from about 2 volumes to about 25 volumes.

17. The processes as claimed in claim 1, wherein the 2-amino-2-(2-(4-octylphenyl)ethyl)-1,3-propanediol or the 2-amino-2-(2-(4-octylphenyl)ethyl)-1,3-propanediol hydrochloride is optionally purified and dried; and wherein the purification is carried out by recrystallization in presence of solvent selected from group comprising toluene, methyl acetate, ethyl acetate, isopropyl acetate, butyl acetate, acetonitrile, methyl isobutyl ketone and methyl ethyl ketone or any combination thereof.

18. The process as claimed in claim 17, wherein volume of the solvent ranges from about 2 to about 30 volumes; wherein temperature for the purification of 2-amino-2-(2-(4-octylphenyl)ethyl)-1,3-propanediol ranges from about 10° C. to about 110° C.; and wherein temperature for the purification of 2-amino-2-(2-(4-octylphenyl)ethyl)-1,3-propanediol hydrochloride ranges from about −25° C. to about 50° C.

19. The process as claimed in claim 17, wherein the drying is carried out under vacuum at temperature ranging from about 20° C. to about 75° C.

20. The process as claimed in claim 1, wherein the compound of Formula 3 is selected from a group comprising 1-(2-iodoethyl)-4-octylbenzene, 1-(2-bromoethyl)-4-octylbenzene, 1-(2-chloroethyl)-4-octylbenzene, 1-(2-ethylmesylate)-4-octylbenzene, 1-(2-ethyltosylate)-4-octylbenzene and 1-(2-ethyltriflate)-4-octylbenzene or any combination thereof.

* * * * *